(12) United States Patent
Hintz et al.

(10) Patent No.: US 8,298,478 B2
(45) Date of Patent: Oct. 30, 2012

(54) METHOD OF PREPARING AN ELECTRODE

(75) Inventors: Michael B. Hintz, Mahtomedi, MN (US); Paul B. Young, New Richmond, WI (US)

(73) Assignee: Medtronic, Inc., Minneapolis, MN (US)

( * ) Notice: Subject to any disclaimer, the term of this patent is extended or adjusted under 35 U.S.C. 154(b) by 666 days.

(21) Appl. No.: 12/429,749

(22) Filed: Apr. 24, 2009

(65) Prior Publication Data
US 2010/0274337 A1    Oct. 28, 2010

(51) Int. Cl.
*B22F 7/08*    (2006.01)

(52) U.S. Cl. ............ 419/8; 361/528; 361/529; 361/508; 361/510

(58) Field of Classification Search ...... 419/8; 361/508, 361/510, 528, 529
See application file for complete search history.

(56) References Cited

U.S. PATENT DOCUMENTS

| | | | |
|---|---|---|---|
| 4,483,819 A | 11/1984 | Albrecht et al. | |
| 4,537,641 A | 8/1985 | Albrecht et al. | |
| 4,574,333 A * | 3/1986 | Snyder | 361/529 |
| 4,945,452 A * | 7/1990 | Sturmer et al. | 361/529 |
| 5,411,571 A | 5/1995 | Kobayashi et al. | |
| 5,699,597 A | 12/1997 | Nakamura et al. | |
| 5,822,177 A | 10/1998 | Popp et al. | |
| 6,447,570 B1 | 9/2002 | Pozdeev-Freeman | |
| 6,819,544 B1 | 11/2004 | Nielsen et al. | |
| 6,876,083 B2 | 4/2005 | Yano et al. | |
| 6,885,548 B2 | 4/2005 | Nyberg | |
| 7,002,790 B2 | 2/2006 | Hossick-Schott et al. | |
| 7,224,576 B2 | 5/2007 | Hossick-Schott | |
| 2002/0071236 A1 | 6/2002 | Yoshida et al. | |
| 2007/0025063 A1 | 2/2007 | Viste et al. | |
| 2008/0145262 A1 | 6/2008 | Freeman et al. | |
| 2009/0279233 A1 * | 11/2009 | Freeman et al. | 361/529 |

FOREIGN PATENT DOCUMENTS
WO    9849356    11/1998

OTHER PUBLICATIONS

P0029676.02 (PCT/US2010/030961) PCT Notification of Transmittal of the International Search Report and the Written Opinion of the International Searching Authority, Mailed Aug. 4, 2010, 11 pages.

\* cited by examiner

*Primary Examiner* — Roy King
*Assistant Examiner* — Ngoclan T Mai

(57) ABSTRACT

Methods of preparing an electrode are provided. A metal powder can be sintered onto a portion of a lead wire to form a connection region. An additional metal powder can be de-oxidation sintered onto the connection region to form the electrode. The oxides formed during the de-oxidation sintering are then removed from the electrode.

13 Claims, 10 Drawing Sheets

METHOD OF PREPARING AN ELECTRODE

FIELD

The present teachings relate to methods for improving mechanical and electrical integrity between the lead wire and anode body in valve-metal anodes. More particularly, the present teachings relate to methods of fabricating anodes using a de-oxidation sintering process.

INTRODUCTION

A porous electrode is formed by pressing and sintering a metal powder to form a porous structure, and a wire is imbedded into the porous structure during pressing to provide a terminal for making electrical connection to the electrode. Pressed and sintered metal powder electrodes are advantageous in a variety of applications as they can exhibit a high surface area to volume ratio relative to electrodes produced by other fabrications methods. One example of a porous electrode comprising a metal powder and a wire or other connection terminal is a valve metal capacitor anode, such as a tantalum capacitor anode.

The sintering process serves to bond the powder particles and powder agglomerates together into a contiguous metallic body and also serves to bond the electrical connection terminal to the porous electrode body formed by the pressed powder. The term sintering as used herein refers to a thermal treatment process wherein the surface area of the sintered body is reduced, as is exemplified by the coarsening of particle size and formation of inter-particle bonds in a sintered metal powder compact. Sintering is typically performed in a furnace at a temperature significantly above room temperature but well below the melting point of the metal powder to maintain a desired level of porosity and microstructural feature size in the final sintered powder compact. For the case of tantalum capacitor anodes, the sintering is typically performed at temperatures ranging from about 1350 degrees Celsius to about 1800 degrees Celsius. This corresponds to temperatures ranging from about 0.5 to 0.62 times the melting temperature of tantalum. Sintering at higher temperatures improves inter-particle bonding but also results in increased shrinkage, reduced porosity, and microstructural feature size coarsening with a corresponding reduction in surface area per unit volume. The choice of sintering temperature is therefore dependent upon the characteristics of the starting powder and the characteristics desired in the finished sintered body.

One class of materials of particular interest for use in porous metal electrodes is the class of metals known as valve metals; the class includes the metals aluminum, tantalum, niobium, titanium, zirconium, and several others. The oxides of all valve metals exhibit a large negative free energy of formation and all valve metals form thin, protective surface oxide films upon exposure to air at room temperature. An additional unique characteristic of valve metals is their ability to form conformal, adherent, electrically insulating metal-oxide films upon anodic polarization in electrically conductive solutions, where the thickness of the metal-oxide films is primarily dependent upon the electrical potential to which the metals are polarized in the conductive solution. The electrical and structural characteristics of porous tantalum electrodes covered with anodically formed amorphous tantalum pentoxide have led to the widespread use of such structures as capacitor anodes, wherein the anodically formed oxide serves as the capacitor dielectric. The processing of tantalum capacitor anodes will be referred to as a non-limiting example.

As noted above, tantalum powders have a great affinity for oxygen and form a thin native surface oxide layer almost immediately upon exposure to an oxygen-bearing environment such as air at ambient temperatures. Due to the thermodynamics of the tantalum-oxygen system, sintering or other thermal processing in high vacuum at temperatures below about 1800 degrees Celsius does not remove oxygen from tantalum metal. In fact, the affinity of tantalum metal for oxygen is such that substantially any thermal processing at elevated temperatures below about 1800 degrees Celsius in substantially any commercially achievable environment (e.g. high vacuum, inert gas, etc.) results in the dissolution of the native surface oxide into the underlying metal, thereby increasing the level of oxygen present in the metal. Re-exposure to an oxygen bearing environment such as exposure to air following thermal treatment re-forms the native surface oxide. Consequently, the oxygen content of the underlying metal continues to increase with each successive thermal treatment.

The performance of sintered metal electrodes in general and valve metal electrodes in particular is often sensitive to contamination. For the case of tantalum capacitor anodes, excessive dissolved oxygen in the tantalum metal underlying the anodically formed amorphous dielectric oxide film is particularly detrimental to capacitor lifetime as it promotes degradation of the dielectric film's structural and electrical properties. Specifically, as the solubility limit for oxygen in the metal is approached, small crystalline oxide phase precipitates form on the surface of the sintered powder compact. These oxide phase precipitates can serve as efficient nuclei for the growth of crystalline oxide into the amorphous oxide formed during the anodization process. Growth of the crystalline oxide phase can disrupt the amorphous oxide film, resulting in increased leakage current and possible failure of the capacitor. Maintaining low oxygen content both during the manufacture of tantalum powder and during its subsequent processing into capacitor anodes is therefore a challenge.

A method for reducing the oxygen content in agglomerated tantalum powders, hereafter known herein as "de-oxidation" is described in U.S. Pat. No. 4,483,819. The method includes heating a mixture of tantalum powder and a metallic reducing agent with a higher affinity for oxygen than tantalum in a vacuum or inert atmosphere and subsequently removing the reaction products and un-reacted reducing agent by leaching in an inorganic acid solution. U.S. Pat. No. 4,483,819 teaches that the described method both reduces the level of oxygen and other impurities in the resulting powder and also reduces leakage current for anodes subsequently prepared from the agglomerated powders relative to prior art agglomerated powders. Significantly, U.S. Pat. No. 4,483,819 also teaches that agglomerated powders produced by the described method can exhibit substantial increases in specific charge, the product of capacitance, C, and the electrical potential used to form the anodic oxide, V, per unit mass of powder, relative to other powder. U.S. Pat. No. 4,483,819 further teaches that magnesium, calcium, and aluminum are suitable reducing agents and that a process temperature range from about 800 degrees Celsius to about 1200 degrees Celsius is preferable for agglomeration. A yet further teaching of U.S. Pat. No. 4,483,819 is that anodes with increased specific charge can be produced directly from a mixture comprising a reducing agent and tantalum powder that has not previously been agglomerated, wherein the de-oxidation process and sintering to final shape and density are substantially combined. Processes combining both a reduction in oxygen content and a substantial reduction in surface area characteristic of sintering will be referred to herein as de-oxidation sintering. The patent claims the processes for producing the reduced-oxygen-content agglomerated powder and capacitor anodes subsequently produced from the reduced-oxygen-content agglomerated powder.

U.S. Pat. No. 4,537,641 extends the teachings of U.S. Pat. No. 4,483,819 to show that it is not necessary to mix the tantalum powder and reducing agent prior to pressing and/or sintering but rather that electrical properties of a previously shaped and/or sintered tantalum anode can be improved by subsequently heating the anode in the presence of a the reducing liquid and/or vapor to temperatures above the melting point of the reducing agent but below the temperatures used for conventional sintering. The patent claims variants of the de-oxidation process for producing capacitor anodes.

U.S. Pat. No. 6,447,570 describes a variant of a combined de-oxidation sintering process for producing porous tantalum and niobium metal pellets for use as capacitor anodes, wherein the process comprises: a) de-oxidizing the porous metal pellets in the presence of a metallic reducing agent; b) subsequently annealing at a temperature above the de-oxidation temperature but below the temperatures typically used for conventional sintering; and c) doping the resulting pellets with nitrogen by reducing the temperature and exposing the pellets to nitrogen gas. All steps are performed consecutively without exposing the pellets to an oxygen containing environment. Exposure to the nitrogen gas following de-oxidation enables the diffusion of nitrogen into the tantalum metal. Nitrogen is much less detrimental to capacitor performance than oxygen but occupies the same intersticial sites in the tantalum lattice. Consequently, the nitrogen doping serves to inhibit the uptake of oxygen upon subsequent exposure to air and is therefore beneficial. U.S. Pat. No. 6,447,570 also teaches that bonding among the pressed powder particles and embedded lead wire typically used to provide an external electrical connection is degraded for anodes processed by previously described de-oxidation sintering methods. Annealing at temperatures above the temperature used for de-oxidation is taught as one means to improve powder particle to lead wire bonding integrity. However, the process as described is disadvantageous from a manufacturing standpoint as the still-present reducing agent contaminates and degrades the annealing furnace at the higher temperatures. U.S. Pat. No. 6,447,570 further teaches pre-sintering a pressed powder body without an embedded lead wire, subsequently welding a lead wire onto the pre-sintered body, and then de-oxidizing the resulting composite structure. This process is also disadvantageous from a manufacturing standpoint due to the additional process steps and associated manufacturing hardware.

More recent publications referring to de-oxidation sintering processes allude to lead wire bonding issues for anodes processed by de-oxidation/sintering, but do not describe any process improvements beyond those mentioned in U.S. Pat. No. 6,447,570 which, as noted previously, are disadvantageous from a manufacturing standpoint.

Many efforts have been made to create a capacitor which is smaller and useful in space critical applications. In the context of space critical applications such as medical devices, capacitors are typically charged and discharged rapidly for delivery of low voltage or high voltage stimuli. Upon or during detection of a potentially lethal arrhythmia, suitable electrical transformer circuitry charges one or more high voltage capacitors using a low voltage battery as a charge source. Then, at an appropriate time the energy stored in the capacitor discharges through a pair of electrodes disposed in or near a patient's heart. The discharged energy is used to terminate the arrhythmia and restore organized cardiac activity.

Medical devices that deliver cardioversion and/or defibrillation therapy include automated external defibrillators (AEDs) and implantable cardioverter-defibrillators (ICDs). An ICD can encompass all such implantable medical devices (IMDs) having at least high voltage cardioversion or defibrillation capabilities. In most all IMDs, energy, volume, thickness and mass are critical features. The batteries and high voltage capacitors used to provide and accumulate the energy required for the effective cardioversion/defibrillation therapy have historically been relatively bulky and expensive. It is recognized that a process known as de-oxidation sintering, where a valve metal powder compact is sintered in the presence of a reactive metal vapor can potentially improve the volumetric energy density (VED) of sintered valve-metal capacitors. However, it is also recognized that a poor electrical connection between the capacitor anode body and lead wire often results for anodes processed by de-oxidation sintering. Known techniques have not adequately addressed the underlying issue of the connection between the lead wire and the anode body for the case of anodes processed by de-oxidation sintering. The present teachings optimize the connection of the anode body to the lead wire and minimize the size of the anode to help facilitate smaller capacitor volumes.

SUMMARY

This section provides a general summary of the teachings, and is not a comprehensive disclosure of its full scope or all of its features.

In various exemplary embodiments, the present teachings provide methods of preparing an electrode. A metal powder can be sintered onto a portion of a lead wire to form a connection region. An additional metal powder can be de-oxidation sintered onto the connection region to form the electrode. The oxides formed during the de-oxidation sintering can then be removed from the electrode. Alternatively, it has been found that processing only the lead wire through de-oxidation prior to embedding the lead wire in the anode body and subsequently de-oxidation sintering the combined lead wire and anode body composite a second time results in an anode body to lead wire connection with greatly improved integrity.

Further areas of applicability will become apparent from the description provided herein. The description and specific examples in this summary are intended for purposes of illustration only and are not intended to limit the scope of the present teachings.

DRAWINGS

The drawings described herein are for illustrative purposes only of selected exemplary embodiments and not all possible implementations, and are not intended to limit the scope of the present teachings.

Corresponding reference numerals indicate corresponding parts throughout the several views of the drawings.

DESCRIPTION OF VARIOUS ASPECTS

Example embodiments will now be described more fully with reference to the accompanying drawings.

The terminology used herein is for the purpose of describing particular example embodiments only and is not intended to be limiting. As used herein, the singular forms "a", "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Figure 1:
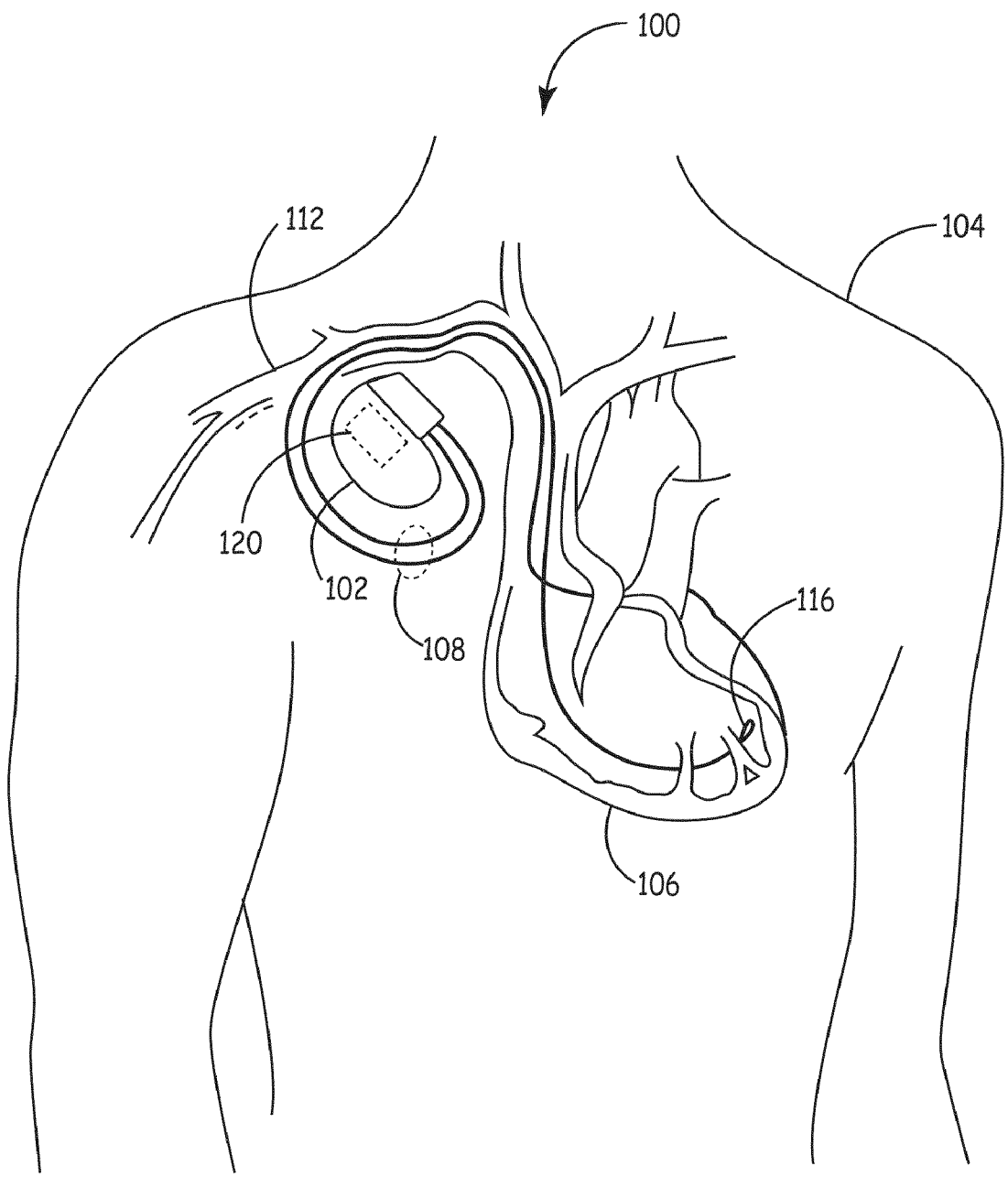
FIG. 1 depicts an implantable medical device in a patient according to various exemplary embodiments.

Turning now to the drawings, and specifically referring to FIG. 1, an implantable medical device (IMD) system 100 which includes an implantable medical device 102, is shown in accordance with one exemplary embodiment of the present teachings. The implantable medical device 102 takes the form of a defibrillator and may be implanted within a patient 104 for providing a therapeutic electric shock to the patient's heart 106. It will be appreciated however, that the implantable medical device 102 may alternatively take the form of various other medical devices including, but not necessarily limited to, a pacemaker, a cardioverter, neural stimulator, drug administering device, etc. without departing from the scope of the present teachings.

The implantable medical device 102 can be housed within a hermetically sealed, biologically inert outer container or housing, which may itself be conductive and also serve as an electrode, if appropriate for the IMD application. One or more leads, collectively identified with reference numeral 108 in FIG. 1, are electrically coupled to the implantable device 102. The leads 108 can extend into the patient's heart 106 via a vein 112. The leads 108 can have one or more exposed conductive electrodes 116 for sensing cardiac activity and/or providing a stimulating voltage to the heart 106.

In accordance with the illustrated exemplary embodiment, the implantable medical device 102 comprises a capacitor bank 120, which includes one or more capacitors (not shown) disposed therein that store energy provided by a battery (not shown) within the implantable medical device 102. In one exemplary embodiment of the present teachings, the capacitor bank 120 stores the energy from the battery to deliver a therapeutic electric shock via the leads 108 to defibrillate the patient's heart 106. That is, when the implantable medical device 102 determines that the cardiac therapy/stimulating electric shock is needed to produce a normal sinus rhythm of the heart 106, the capacitors in the capacitor bank 120 are charged to a pre-determined charge level by the battery. When the implantable medical device 102 determines that a therapeutic electric shock is needed, the charge stored in the capacitors is released by discharging the capacitors of the capacitor bank 120 through the patient's heart tissue via the leads 108.

Figure 2:
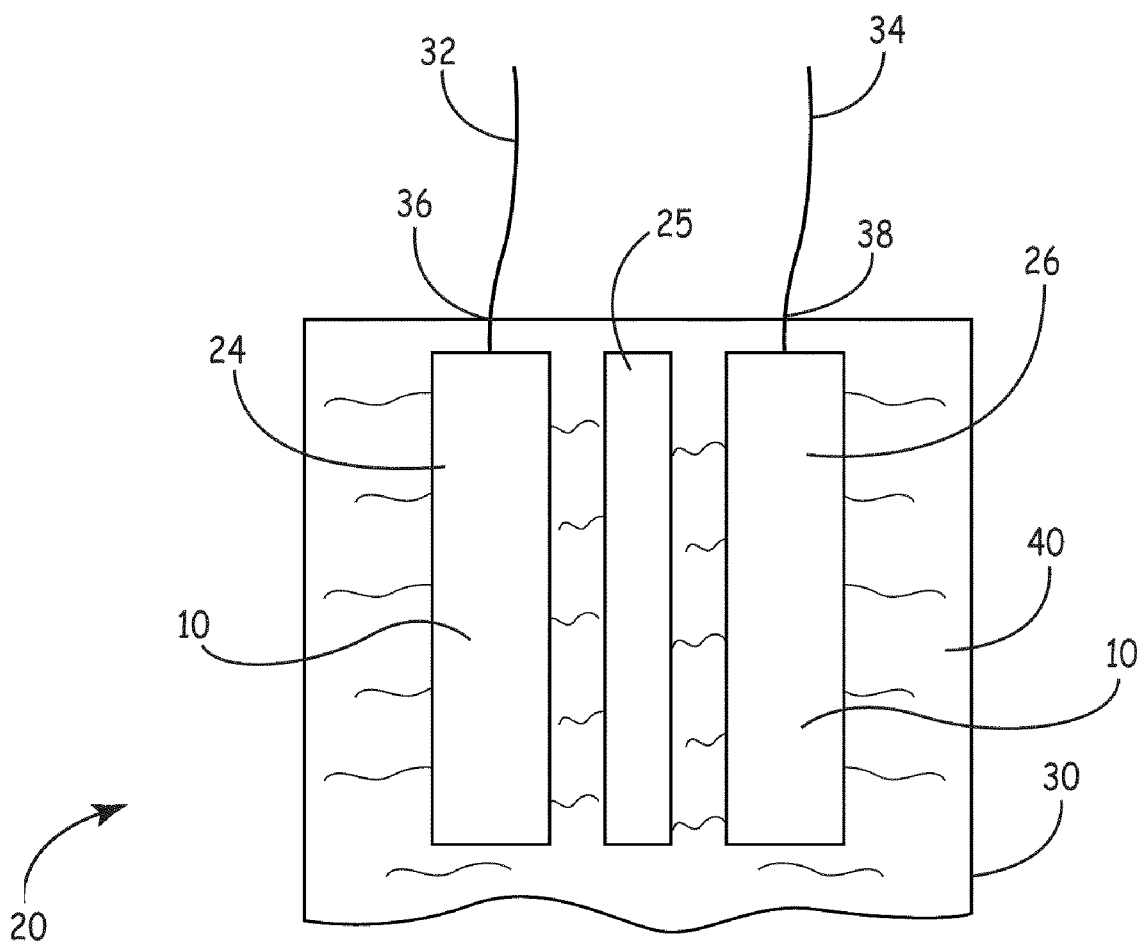
FIG. 2 depicts a capacitor according to various exemplary embodiments.
Figure 3:
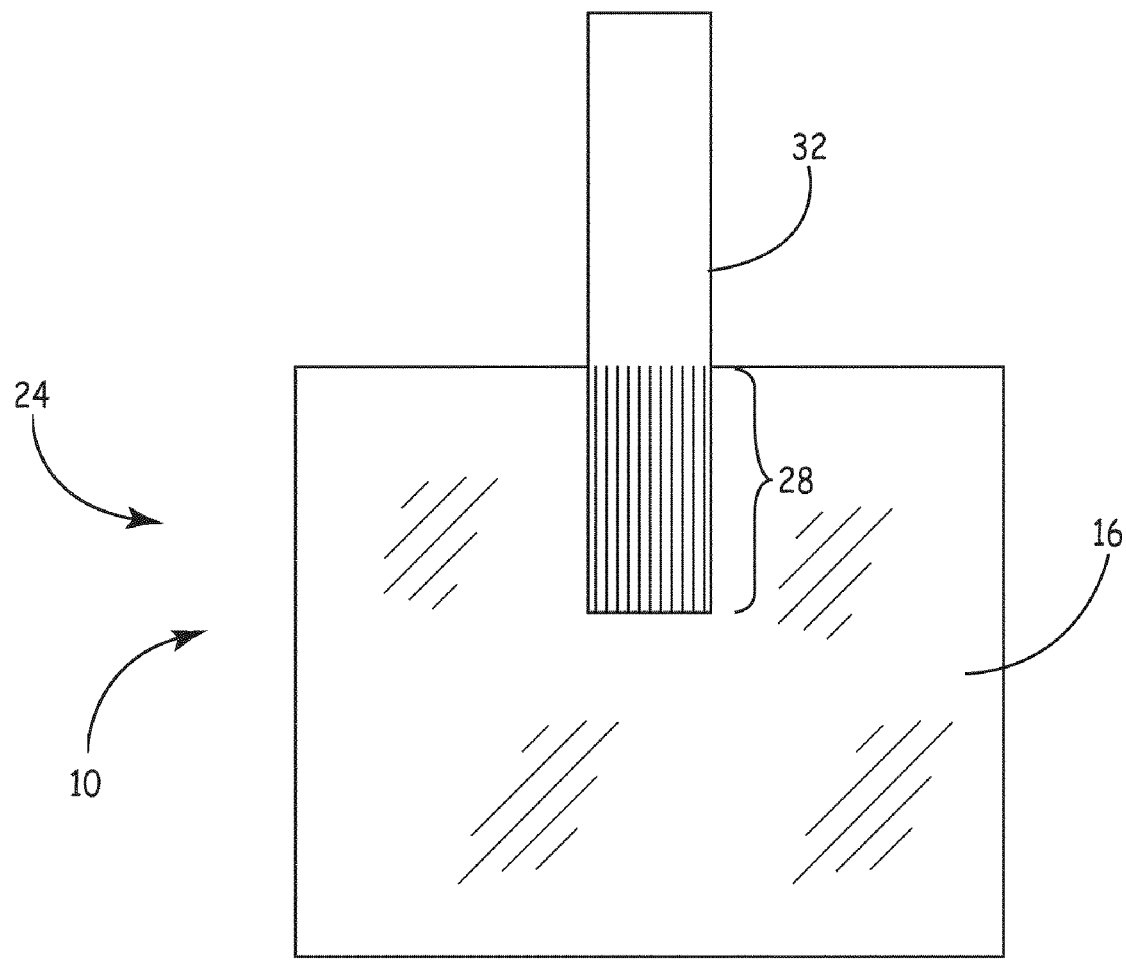
FIG. 3 depicts an anode according to various exemplary embodiments.

Referring to FIGS. 2 and 3, in various exemplary embodiments, the present teachings provide methods of forming an electrode 10. With specific reference to FIG. 2, the electrodes 10 are disclosed in connection with a capacitor assembly 20. The capacitor assembly 20 can be assembled from an anode 24, a cathode 26, and a separator 25 between the anode 24 and the cathode 26 and fitted into the capacitor case 30 with appropriate electrical connectors 32, 34 to the anode 24 and cathode 26. In other exemplary embodiments, a capacitor 20 can be assembled from the anode 24, a cathode 26, and a separator 25 between the anode 24 and the cathode 26, and a plurality of the layers 24, 26 are stacked into a capacitor sub-assembly, electrically interconnected and fitted into a capacitor case 30 with appropriate electrical connectors 32, 34 to the anode 24 and cathode 26. The electrodes 10 of the present teachings are able to carry a high voltage of from about 150 to about 375 volts.

The anode 24 can be electrically coupled to an anode lead wire 32 or pin. The anode lead wire 32 passes through the inner and outer surfaces of the capacitor case 30 via a feed-through 36. The cathode 26 can be similarly coupled to a cathode lead 34 which passes through the inner and outer surfaces of the capacitor case 30 via a feed-through 38. Alternatively, the capacitor case 30 may be used as an electrical connection in the cathode 26. The capacitor case 30 can be filled with a fluid electrolyte 40 which provides a current path between the anode 24 and the cathode 26. It is understood that although the present teachings provide a more detailed description of the anode 24, it is understood that the present teachings can be applied to formation of the cathode 26 as well.

The anode 24 of the present teachings further comprises an anode body 16. The various parts of the anode 24 can be made of any suitable metal including, but not limited to, aluminum, tantalum, niobium, titanium, zirconium, etc., all of which form adherent, electrically insulating metal-oxide films upon anodic polarization in electrically conductive solutions. Combinations of the above-identified materials and others are also within the scope of the present teachings.

Figure 4:
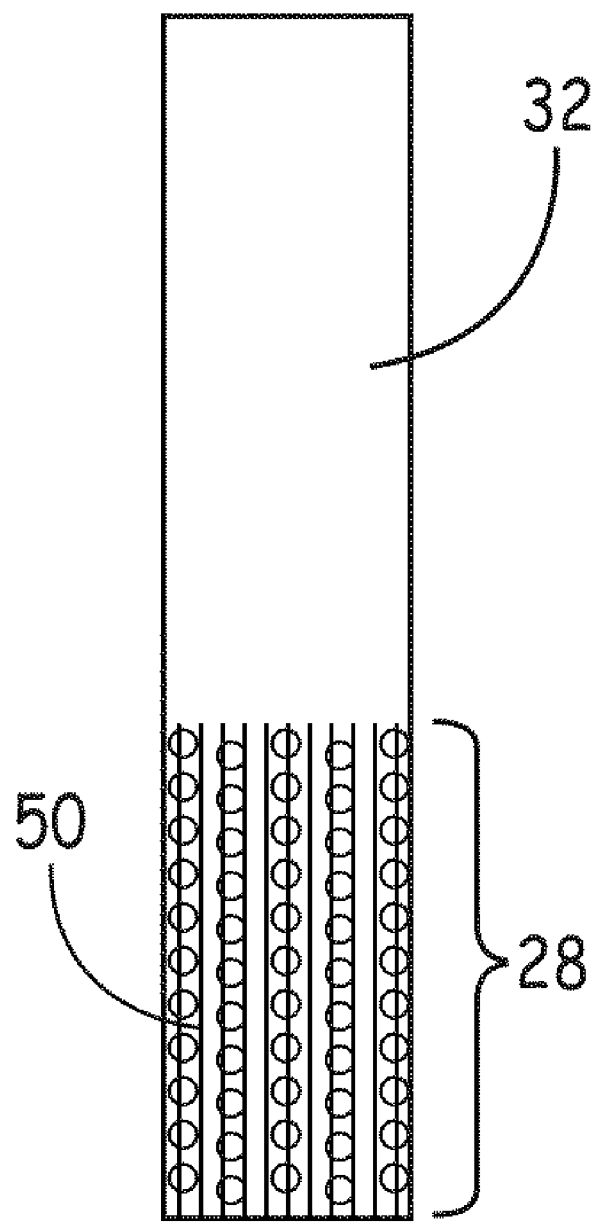
FIG. 4 depicts a lead wire having a connection region sintered thereon according to various exemplary embodiments.

Referring to FIGS. 3 and 4, the lead wire 32 can be pretreated to improve subsequent bonding to the anode body 16. A small volume of metal powder 50 is applied to the lead wire 32 and subsequently vacuum sintered onto a portion of the lead wire 32. In various exemplary embodiments, this sintering can be conducted at a temperature of above 1100 degrees C., more particularly from about 1350 degrees C. to about 1600 degrees C. In certain exemplary embodiments, the sintering can be conducted at a temperature of about 1550 degrees C. The temperature can be modified depending on the materials, but is conducted at a sufficiently low temperature to substantially retain the metal powder morphology. The particulate metal 50 can be applied to the lead wire 32 in the form of a metal powder or as a slurry. The particulate metal 50 can be applied to a region of the lead wire 32 to form a contact region 28. As illustrated, the contact region 28 can be formed up a discrete length of the lead wire 32 as this portion will be embedded in the anode 24.

In one embodiment, after sufficient application of the particulate metal 50, the coated, unsintered lead wire 32 (or green wire) can be placed in a die to compress the particulate metal 50 around the lead wire 32 to form a compact. The powder compact exhibits sufficient strength to enable easy handling and placement in the vacuum sintering furnace. It is understood that the die to form the contact region 28 can be much smaller than a die used to form the anode body 16. The lead wire 32 and particulate metal 50 within the die can then be subjected to a vacuum sintering process, where heat is applied in a high vacuum environment, to adhere the particulate metal 50 at the contact region 28. This forms a "prepared" lead wire or pin 32. The prepared lead wire 32 with the contact region 28 provides a better interface and substrate to which to adhere the anode body 16. This increases the success of the subsequent processing steps necessary to produce a functional capacitor and increases overall production process yields for anodes processed using de-oxidation sintering.

In various exemplary embodiments, pre-treatment of the lead wire 32 to improve subsequent bonding to anode body 16 during de-oxidation sintering is accomplished by de-oxidizing lead wire 32 by itself prior to embedding it into the anode body 16. In such exemplary embodiments, the lead wire 32 can be placed in a chamber 60 for de-oxidation.

De-oxidation sintering differs from the traditional type sintering referenced above as de-oxidation sintering can be conducted at a lower temperature, in a selected gaseous environment, and the metal bonding can be slightly different as will be detailed later herein. Applicants have found that the de-oxidation sintering process facilitates forming smaller capacitors for space-critical applications which are capable of handling high voltage and is therefore beneficial. A problem in using de-oxidation sintering has been the establishment of a proper bond between anode and the lead wire The complicated methods used to overcome this problem with other lead wire to anode body bonding techniques are a primary disincentive to the use of de-oxidation sintering for electrode production. The present teachings provide straightforward solutions to the lead wire-anode body bonding problem and thereby significantly enhance manufacturability of electrodes processed by de-oxidation sintering.

Figure 5A:
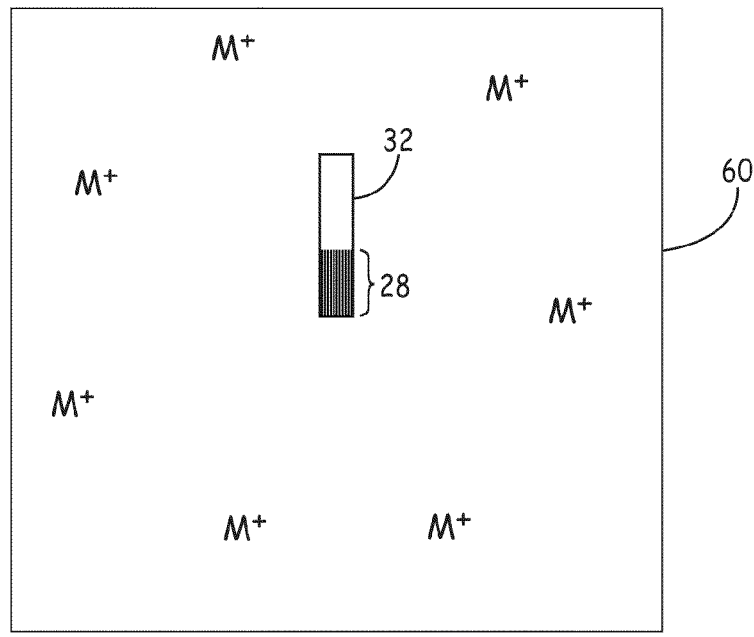
FIG. 5A depicts a de-oxidation sintering process of a lead wire according to various exemplary embodiments.

De-oxidation and de-oxidation sintering comprise applying heat and pressure in a metal vapor (M+) atmosphere. For example, the de-oxidation sintering of tantalum capacitor anodes can be conducted at a temperature of about 1150 degrees C. This temperature is significantly lower than the 1350 to 1600 degrees C. temperature used in the traditional vacuum sintering process detailed above. As shown in FIG. 5A (and also FIG. 5B as detailed later herein), the de-oxidation sintering can be conducted in a vessel 60, which in various embodiments can be a substantially hermetic vessel, in the presence of a metal vapor, indicated by the symbol $M^+$. The metal which forms the metal vapor atmosphere generally has a higher affinity for oxygen than the particulate metal 50 used for the anode 24. For example, if the metal 50 comprises tantalum, the metal vapor could comprise a metal having a higher affinity for oxygen. In various exemplary embodiments, the metal vapor atmosphere is selected from the group consisting of magnesium and calcium.

The de-oxidation sintering facilitates production of an anode 24 with a more uniform particle size distribution than is obtainable by conventional vacuum sintering of commercially available powders. Under appropriate conditions the more uniform particle size obtainable by de-oxidation sintering can result in a capacitor anode 24 exhibiting significantly greater capacitance per unit volume than is obtained by conventional vacuum sintering.

Due to the presence of the reactive metal vapor M+, an oxide layer or particles may forms on the electrode surface. For example, a magnesium oxide layer can form where a magnesium vapor can be used in the de-oxidation sintering process. To remove the oxide layer, the electrode 10 can be subjected to an acid treatment. The acid treatment, such as a bath, dip, or spray removes the oxides without damaging the underlying substrate. Suitable acids for the treatment include weak solutions of an inorganic acid, such as hydrochloric acid, as a non-limiting example. The washing can be followed with a rinse using de-ionized water, for example, and a subsequent drying.

Figure 5B:
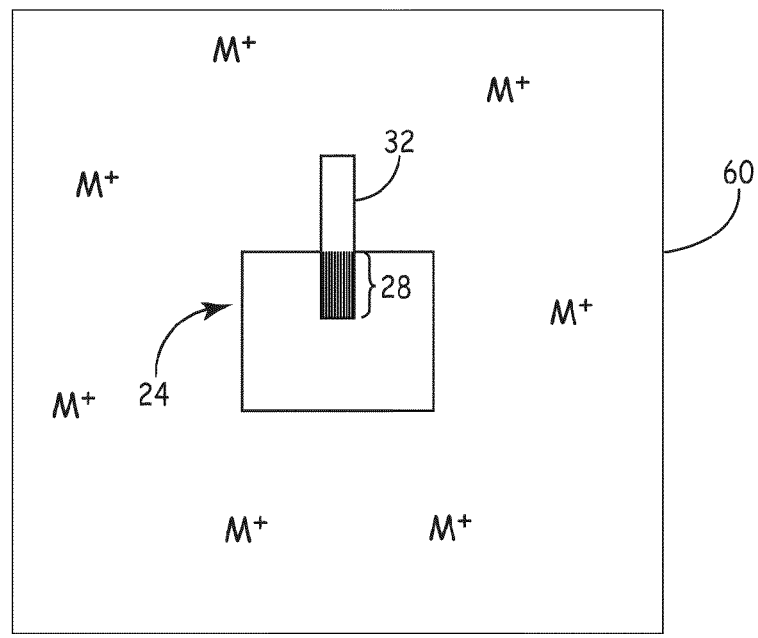
FIG. 5B depicts a de-oxidation sintering process of an electrode onto a lead wire according to various exemplary embodiments.

Whether the pin or lead wire 32 pre-treatment is performed using a traditional sintering technique or a de-oxidation technique, the pre-treated pin 32 can then be pressed into the powder for the anode body 16 and ultimately the anode 24. The anode body 16 can be formed by building up additional or second powdered metal onto the prepared lead pin 32. The second or subsequent metal powder or slurry can be applied over the contact region 28 and subjected to a de-oxidation sintering process as shown in FIG. 5B. The de-oxidation sintering secures the second metal which forms the anode body 16 over the prepared lead wire 32. The same metal or at least one different metal can be used to form the anode body 16 and the contact region 28.

After completion of the de-oxidation sintering process the surface of the anode 24 can be cleaned to remove the reactive metal oxides formed during processing. In order to produce a functional capacitor anode it is generally necessary to subsequently form an anodic oxide on the surface of the sintered metal compact by anodically polarizing the metal compact in a suitable electrolyte. Production of a high quality capacitor anode may comprise a first anodic oxide formation step, a thermal treatment or annealing process, and a second anodic oxide formation step, as is well known in the electrolytic capacitor art.

Referring to FIG. 1, the various electrodes 10 and capacitors 20 formed according to the present teachings are useful in several space-critical applications. As a non-limiting example, an anode 24 can be incorporated into a capacitor 20 which can be connected to the implantable medical device system 100. A therapy can then be administered from the implantable medical device system 100 to the patient. The therapy can include exposing the capacitor to a voltage of from between 150 to 375 volts, and all sub-ranges in between. An exemplary therapy is treatment of an arrhythmia.

EXAMPLES

The following examples are prepared according to the present teachings. Certain exemplary embodiments illustrated below have increased adherence of the anode body 16 to the lead wire 32. The improved anode body to lead wire 32 adherence (bonding) results in improved overall process yield for anode production and improved electrical performance of the resulting anodes.

Comparative Example

Figure 6:
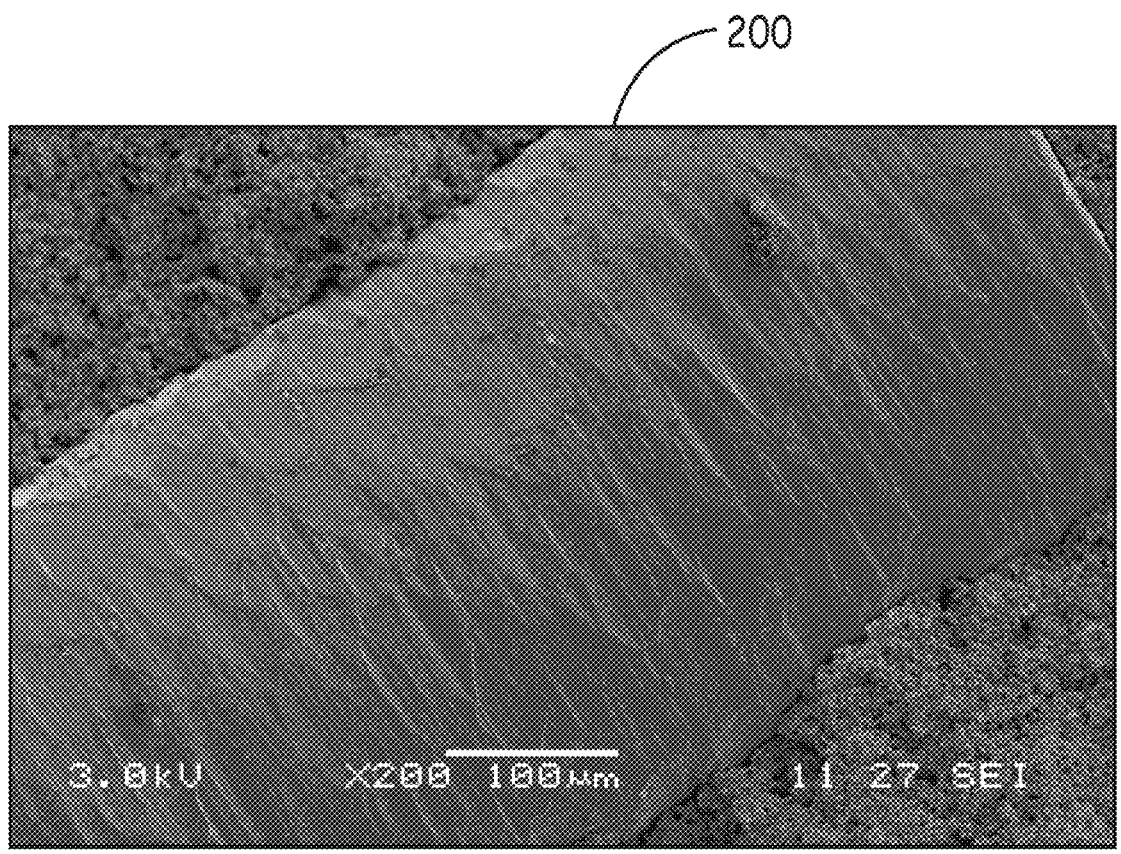
FIG. 6 depicts the surface of a reference lead wire which was embedded in a test anode and subsequently processed through de-oxidation sintering, processing, leaching, and formation.

One of ten as-received centerless-ground lead wires 200 is represented in FIG. 6. The lead wires were pressed into a tantalum powder body to form test anodes and were processed through de-oxidation sintering and acid leaching. An attempt was then made to form an anodic oxide up to a formation potential of 260V. Two of the test anodes including untreated lead wires 200 failed second formation or forming an anodic oxide capable of withstanding the desired 260V formation potential. Eight of the test anodes were successfully formed to a potential of 260V. However, one of the test anodes which included untreated lead wires 200 exhibited more than a five-fold increase in the equivalent series resistance (ESR) as compared to the lot average. This indicated poor electrical connection between the anode body and lead wire.

Experimental Example

Twenty, as-received, centerless-ground anode lead wires 300 or pins were processed through a de-oxidation process in the presence of magnesium vapor at 1170 degrees C. to provide "pre-deoxidized" (PDO) lead wires 300. The PDO pins 300 were then leached in a solution consisting of 6N sulfuric acid+3 vol. % of 28-32% hydrogen peroxide for over four hours. The PDO pins were subsequently washed in deionized water and dried. NH175 and NA30KN powders (Available from H.C. Starck, Cincinnati, Ohio, USA) were then used to dry press test anodes using PDO pins. The resulting green anodes were processed by de-oxidation sintering at 1170 degrees C. for six hours in the presence of 2.8 g of Mg pellets. The resultant anodes were leached to remove the magnesium oxides, rinsed, dried, and sent through a anodic oxide formation process identical to those employed in the Comparative Example up to a potential of 260V. The resultant capacitor formed with the anode was charged to 255V in working electrolyte.

Yield through working electrolyte charging (WEC) for the first ten of the twenty anodes comprising PDO pins was 100%. Three additional de-oxidation sintering runs employing anodes comprising PDO pins were done over the course of roughly 4 weeks. Overall yield through WEC for all four runs using PDO pins was greater than 97%. This result improved the overall yield relative to any previous groups of experimental anodes processed by de-oxidation sintering.

Figure 7:
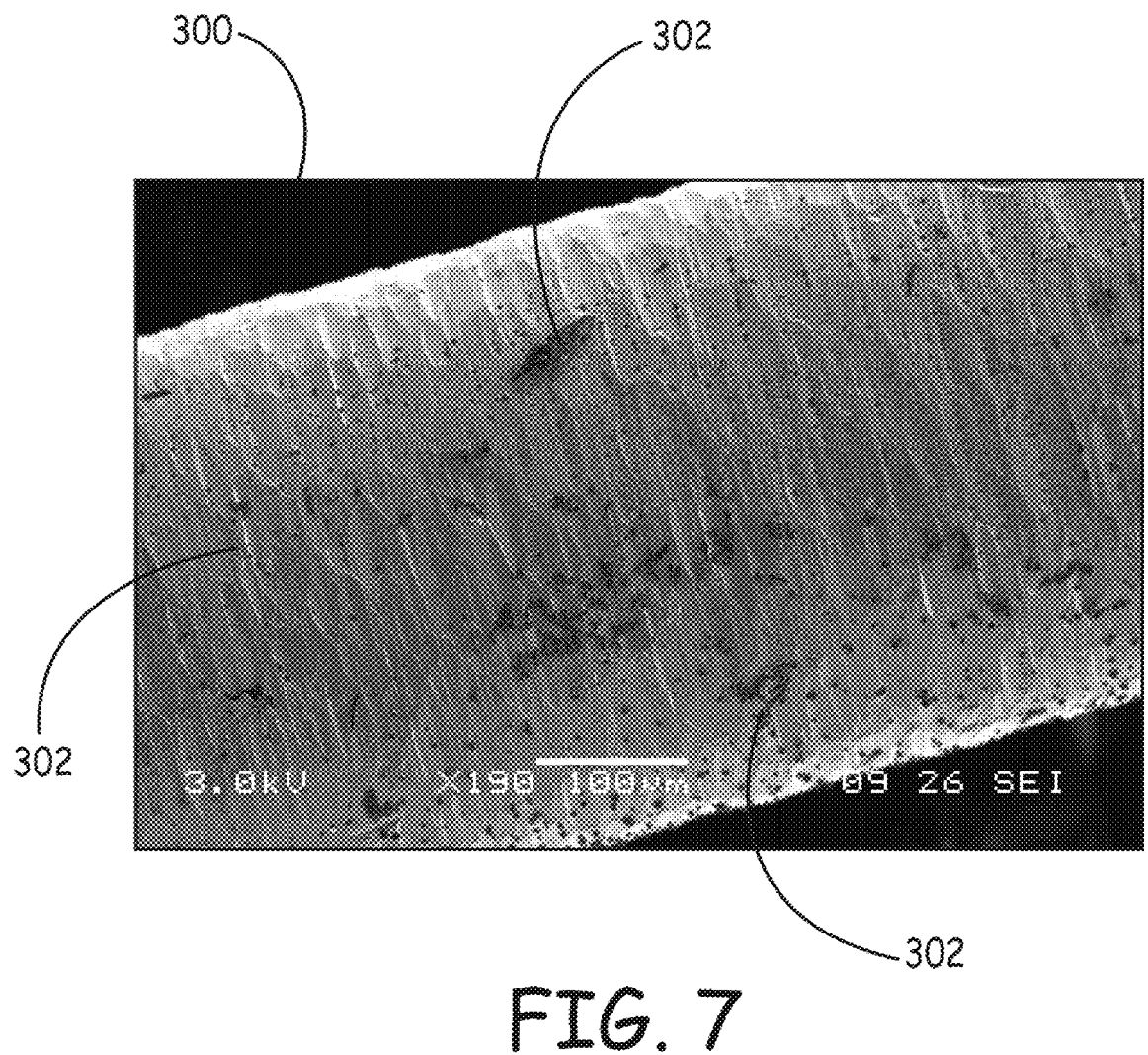
FIG. 7 depicts the surface of a lead wire immediately after de-oxidation sintering only the wire.
Figure 8:
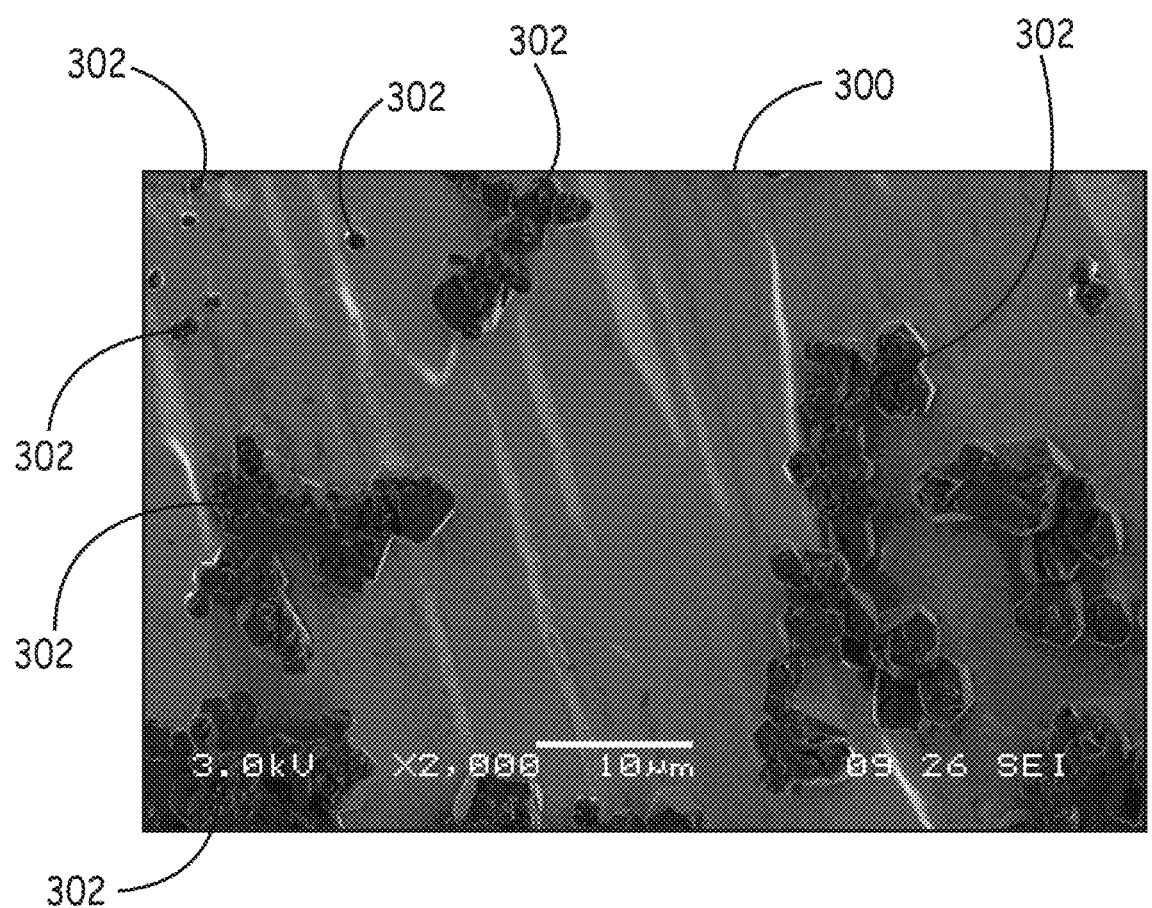
FIG. 8 depicts an enlarged view of the surface of a lead wire immediately after de-oxidation sintering of FIG. 7.
Figure 9:
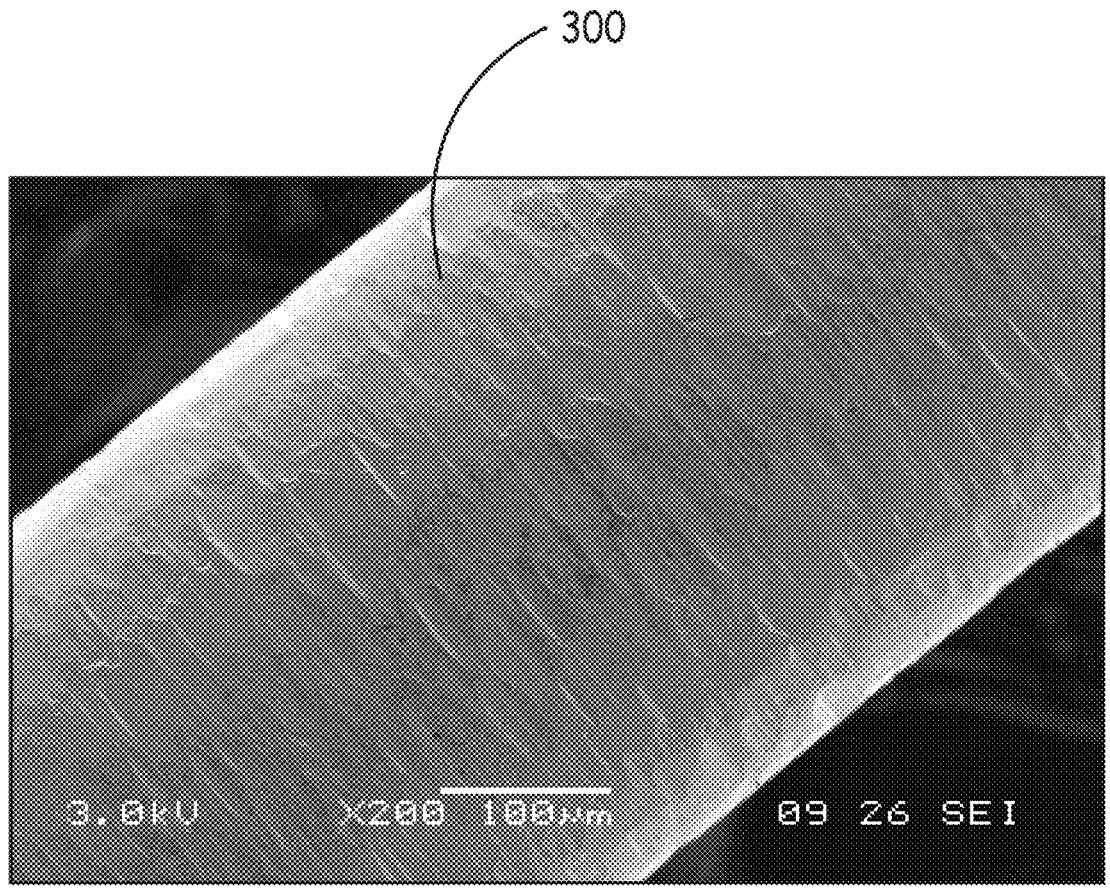
FIG. 9 depicts the surface of a lead wire after oxide removal.

FIG. 7 shows the surface of a standard pin following a de-oxidation process but before leaching. A very high density of magnesium oxide (MgO) crystallites 302 can be seen on the surface of the lead wire 300. FIG. 8 depicts a region of FIG. 7 at a higher magnification, where the morphology of the MgO crystallites 302 is evident. It is believed to be likely that these crystallites 302 were formed by coagulation of a quasi-continuous film of MgO that formed on the surface at a relatively early stage of the de-oxidation process as the (presumably relatively uniformly distributed) oxygen in the lead wire 300 reacted with magnesium liquid or vapor arriving at the lead wire 300 surface. As can be seen in FIG. 9, the leaching process removes substantially all of the MgO crystallites. As noted previously, it is believed to be likely that the formation of a MgO film on the lead wire 300 surface is likely to inhibit good bonding of the surrounding powder to the pin surface. The oxygen content of as-received and PDO lead wires were compared using secondary ion mass spectrometry (SIMS). Dynamic SIMS analysis employing cesium primary ions reveals that the sub-surface oxygen content of a PDO lead wire is about twenty or more times lower than the sub-surface oxygen content of an as-received lead wire. These data support the belief that PDO lead wires form less surface magnesium oxide during the subsequent de-oxidation sintering processes employed to produce the porous anode-lead wire composite structure.

Figure 10:
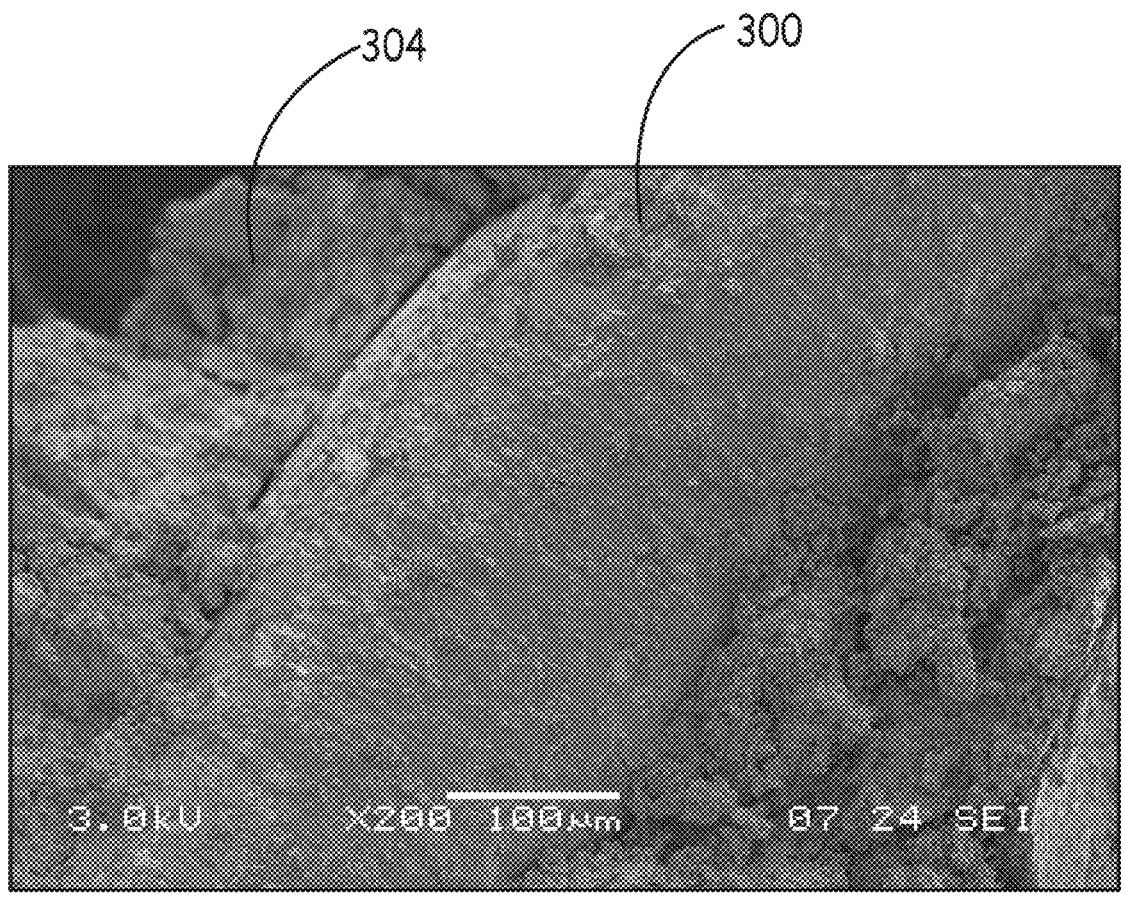
FIG. 10 depicts the surface of a pin that has been processed through de-oxidation sintering and leaching prior to embedding in the pressed powder anode body and subsequently reprocessed through de-oxidation sintering, leaching, and formation.

FIG. 10 depicts the surface of a PDO lead wire 300 that was pressed into a test anode following de-oxidation sintering processing and formation. The anode body 304 was mechanically broken away to reveal the lead wire 300 surface. It is clear that residue and clusters of sintered powder remain bonded to the pin surface. In contrast, the comparative example shown in FIG. 6 shows the surface of an as-received pin that was pressed into a test anode and subsequently processed through de-oxidation sintering and formation under the same conditions as the PDO pin 300 of FIG. 10. The lead wire 200 of FIG. 6 shows very little bonding of the powder to the lead wire 200.

The overall yield through charging of the ten anodes represented by FIGS. 9 and 10 was 100% and all exhibited low ESR as determined by impedance spectroscopy.

The foregoing description of the exemplary embodiments has been provided for purposes of illustration and description. It is not intended to be exhaustive or to limit the teachings. Individual elements or features of a particular exemplary embodiment are generally not limited to that particular exemplary embodiment, but, where applicable, are interchangeable and can be used in a selected exemplary embodiment, even if not specifically shown or described. The same may also be varied in many ways. Such variations are not to be regarded as a departure from the teachings, and all such modifications are intended to be included within the scope of the teachings.

What is claimed is:

1. A method of preparing an electrode for a medical device comprising:
    a. pre-treating a region of an electrically conductive lead wire;
    b. de-oxidation sintering a metal powder compact comprising the lead wire embedded in a metal powder in the presence of a reactive metal vapor wherein the lead wire and metal powder become bonded together during the de-oxidation sintering, wherein the pre-treating improves bonding of the metal powder compact to the lead wire and comprises pre-bonding a small quantity of the metal powder to a portion of the lead wire using conventional vacuum sintering at a temperature higher than that used for the de-oxidation sintering process; and
    c. removing reactive metal oxides formed during the de-oxidation sintering process.

2. The method of claim 1, wherein the reactive metal vapor has a higher oxygen affinity than the metal powder.

3. The method of claim 1, wherein the metal vapor atmosphere is selected from the group consisting of magnesium and calcium.

4. The method of claim 1, further comprising conducting the de-oxidation sintering at a temperature greater than 1100 degrees C.

5. The method of claim 1, wherein removing oxides from the electrode comprises leaching the oxides in an acid bath.

6. The method of claim 1, wherein the metal powder comprises tantalum powder.

7. The method of claim 1, wherein the electrode comprises a capacitor anode.

8. A method of preparing an electrode for a medical device comprising:
   a. pre-treating a region of an electrically conductive lead wire;
   b. de-oxidation sintering a metal powder compact comprising the lead wire embedded in a metal powder in the presence of a reactive metal vapor wherein the lead wire and metal powder become bonded together during the de-oxidation sintering, wherein the pre-treating improves bonding of the metal powder compact to the lead wire and comprises pre-bonding a small quantity of the metal powder to a portion of the lead wire using conventional vacuum sintering at a temperature greater than 1350 C. but less than 1600 C.; and
   c. removing reactive metal oxides formed during the de-oxidation sintering process.

9. The method of claim 8, wherein the reactive metal vapor has a higher oxygen affinity than the metal powder.

10. The method of claim 8, wherein the metal vapor atmosphere is selected from the group consisting of magnesium and calcium.

11. The method of claim 8, wherein removing oxides from the electrode comprises leaching the oxides in an acid bath.

12. The method of claim 8, wherein the metal powder comprises tantalum powder.

13. The method of claim 1, wherein the electrode comprises a capacitor anode.

* * * * *